United States Patent [19]
Owaga et al.

[11] Patent Number: 5,707,639
[45] Date of Patent: Jan. 13, 1998

[54] SOLID INSECT GROWTH REGULATING COMPOSITIONS

[75] Inventors: Masao Owaga, Osaka-fu; Masao Inoue; Toshiro Ohtsubo, both of Hyogo-ken; Hitoshi Kawada, Osaka-fu, all of Japan

[73] Assignee: Sumitomo Chemical Company, Limited, Osaka, Japan

[21] Appl. No.: 323,665

[22] Filed: Oct. 17, 1994

[30] Foreign Application Priority Data

| Oct. 18, 1993 | [JP] | Japan | 5-259663 |
| Dec. 27, 1993 | [JP] | Japan | 5-333790 |
| Mar. 1, 1994 | [JP] | Japan | 6-031364 |
| May 31, 1994 | [JP] | Japan | 6-118809 |

[51] Int. Cl.$^6$ ............................. A01N 25/10
[52] U.S. Cl. ........................ 424/409; 424/419
[58] Field of Search .................. 424/409; 514/345

[56] References Cited

U.S. PATENT DOCUMENTS

| 4,473,582 | 9/1984 | Greene | 514/531 |
| 5,196,408 | 3/1993 | Fahmy et al. | 514/80 |
| 5,300,293 | 4/1994 | Minagawa et al. | 424/405 |
| 5,340,804 | 8/1994 | Wickiser | 514/150 |
| 5,391,370 | 2/1995 | Roe et al. | 424/78.37 |

Primary Examiner—Peter F. Kulkosky
Attorney, Agent, or Firm—Sughrue, Mion, Zinn, Macpeck & Seas, PLLC

[57] ABSTRACT

There is disclosed an insect growth regulator composition comprising (a) an insect growth-regulating active ingredient and, if necessary, another insecticidal active ingredient, (b) an organic substance having a solubility of not greater than 2% in water at 20° C. and a melting point of 35° through 100° C., and (c) a glycol selected from the group having a melting point of 35° through 100° C. and consisting of polyethylene glycol, polyoxyethylene polyoxypropylene glycol, polyoxyethylene polyoxybutylene glycol, and polyoxyethylene polyoxypropylene polyoxybutylene glycol, wherein the weight of the constituent (b) is equal to or greater than 3% based on the total weight, and a sum of the weight of the constituent (b) and the weight of the constituent (c) ranges from 20 to 98% based on the total weight, the constituent (b) and the constituent (c) being molten and then cooled to be solidified in manufacturing process of the insect growth regulator composition. The composition of the invention is the labor- and cost-saving composition because it releases an active ingredient gradually, and exterminates harmful and/or offensive pests and prevent the breeding thereof in water systems over a long time.

16 Claims, 2 Drawing Sheets

SOLID INSECT GROWTH REGULATING COMPOSITIONS

The present invention relates to a novel insect growth regulating composition having prolonged action.

An emulsifiable pesticidal solid composition having pesticidal effects and containing polyethylene glycol is disclosed in Japanese Patent Application Laid-Open No. 90-279604.

Nature has various water systems such as rivers, ponds, swamps, canals, and puddles whereas there are also artificial water systems such as drainages of bath tubs and flush toilets. A variety of harmful and/or offensive insects are bred in such water systems. Since these pests are successively bred in the water systems, prolonged action of active ingredients is required to efficiently prevent breeding of the pests.

The emulsifiable pesticidal solid composition described above has high flowability and is thus easily emulsified in water, which causes the active ingredient to flow out with water in water systems. The known composition accordingly does not exert sufficient effects in places requiring prolonged action.

As a result of extensive study, the inventors have found that a certain solid composition containing an insect growth-regulating active ingredient gives a labor- and cost-saving composition having prolonged action to prevent breeding of the harmful and/or offensive pests and exterminate them in water systems over a long period of time.

The invention relates to an insect growth regulating composition (hereinafter referred to as 'composition of the invention') comprising (a) an insect growth-regulating active ingredient and, if necessary, another insecticidal active ingredient, (b) an organic substance having a solubility of not greater than 2% in water at 20° C. and a melting point of 35° through 100° C., and (c) a glycol selected from the group having a melting point of 35° through 100° C. and consisting of polyethylene glycol, polyoxyethylene polyoxypropylene glycol, polyoxyethylene polyoxybutylene glycol, and polyoxyethylene polyoxypropylene polyoxybutylene glycol, wherein the weight of the constituent (b) is equal to or greater than 3% based on the total weight, and the sum of the weight of the constituent (b) and the weight of the constituent (c) ranges from 20 to 98% based on the total weight, the constituent (b) and the constituent (c) being molten and then cooled to be solidified in manufacturing process of the insect growth regulator composition.

The insect growth-regulating active ingredient contained in the composition of the invention is not restricted specifically, and examples of it are juvenile hormone-like compounds such as dodecadienoates, oxim ether compounds, pyridyl ether compounds and carbamates, and chitin inhibitor such as benzoylphenylurea compounds, and geometrical and optical isomers thereof. Typical examples are given below with reference numbers:

(1) isopropyl(2E-4E)-11-methoxy-3,7,11-trimethyl-2,4-dodecadienoate <Methoprene>;
(2) ethyl(2E-4E)-3,7,11-trimethyldodeca-2,4-dienoate <Hydroprene>;
(3) 2-[1-methyl-2-(4-phenoxyphenoxy)ethoxy]pyridine <Pyriproxyfen>;
(4) propionaldehyde oxime 0-2-(4-phenoxyphenoxy)ethyl ether;
(5) propionaldehyde oxime 0-2-(4-phenoxyphenoxy)propyl ether;
(6) O-ethyl N-[2-(4-phenoxyphenoxy)ethyl]carbamate <Fenoxycarb>;
(7) 1-(4-ethylphenoxy)-6,7-epoxy-3,7-dimethyl-2-octene <R-20458>;
(8) 1-(4-chlorophenyl)-3-(2,6-difluorobenzoyl)urea <Diflubenzuron>;
(9) 2-chloro-N-[[[4-(trifluoromethoxy)-phenyl]amino]carbonyl]benzamide <Triflumuron>;
(10) N-[[[5-(4-bromophenyl)-6-methyl-2-pyrazinyl]amino]carbonyl]-2,6-dichlorobenzamide <EL 494>;
(11) 1-(3,5-dichloro-2,4-difluorophenyl)-3-(2,6-difluorobenzoyl)urea <Teflubenzuron>;
(12) 1-[3,5-dichloro-4-(3-chloro-5-trifluoromethyl-2-pyridyloxy) phenyl]-3-(2,6-difluorobenzoyl)urea <Chlorfluazuron>;
(13) N-[[[3,5-dichloro-4-(1,1,2,2-tetrafluoroethoxy)phenyl]amino]carbonyl]-2,6-difluorobenzamide <XRD-473>;
(14) 1-(2,6-difluorobenzoyl)-3-[2-fluoro-4-(1,1,2,2-tetrafluoroethoxy) phenyl]urea; and
(15) 1-(2,6-difluorobenzoyl)-3-(2-fluoro-4-trifluoromethylphenyl) urea.

Another insecticidal active ingredient may be mixed with the insect growth-regulating active ingredient at an arbitrary ratio. Typical examples of the insecticidal active ingredient are pyrethroids, organophosphorus compounds, carbamates, chloropyridine compounds, and insecticidal proteins as shown below:

(16) 5-benzyl-3-furylmethyl chrysanthemate;
(17) 5-benzyl-3-furylmethyl (1R)-chrysanthemate;
(18) 3,4,5,6-tetrahydrophthalimide methyl chrysanthemate;
(19) 3,4,5,6-tetrahydrophthalimide methyl (1R)-chrysanthemate;
(20) 3-phenoxybenzyl chrysanthemate;
(21) 3-phenoxybenzyl (1R)-chrysanthemate;
(22) 3-phenoxybenzyl 3-(2,2-dichlorovinyl)-2,2-dimethylcyclopropane carboxylate;
(23) 3-allyl-2-methyl-4-oxocyclopent-2-enyl chrysanthemate;
(24) 3-allyl-2-methyl-4-oxocyclopent-2-enyl (1R)-chrysanthemate;
(25) 1-ethynyl-2-methyl-2-pentenyl (1R)-chrysanthemate;
(26) 1-ethynyl-2-methyl-2-pentenyl 2,2,3,3-tetramethyl cyclopropanecarboxylate;
(27) (S)-2-methyl-4-oxo-3-(2-propynyl)cyclopent-2-enyl (1R)-chrysanthemate;
(28) α-cyano-3-phenoxybenzyl chrysanthemate;
(29) α-cyano-3-phenoxybenzyl (1R)-chrysanthemate;
(30) 3-allyl-2-methyl-4-oxocyclopent-2-enyl 2,2,3,3-tetramethylcyclopropanecarboxylate;
(31) 2,3,5,6-tetrafluorobenzyl (1R)-trans-3-(2,2-dichlorovinyl)-2,2-dimethylcyclopropanecarboxylate;
(32) 2,3,5,6-tetrafluoro-4-methylbenzyl 3-(2,2-dichlorovinyl)-2,2-dimethylcyclopropanecarboxylate;
(33) (S)-α-cyano-3-phenoxybenzyl (1R,3S)-2,2-dimethyl-3-(1,2,2,2-tetrabromoethyl)cyclopropanecarboxylate;
(34) α-cyano-3-phenoxybenzyl 2-(4-chlorophenyl)-3-methylbutylate;
(35) (S)-α-cyano-3-phenoxybenzyl (S)-2-(4-chlorophenyl)-3-methylbutylate;
(36) α-cyano-3-phenoxybenzyl 2,2,3,3-tetramethylcyclopropanecarboxylate;
(37) α-cyano-3-phenoxybenzyl 3-(2,2-dichlorovinyl)-2,2-dimethylcyclopropanecarboxylate;
(38) α-cyano-3-phenoxybenzyl 2-(2-chloro-4-trifluoromethylanilino)-3-methylbutylate;
(39) 2-(4-ethoxyphenyl)-2-methylpropyl 3-phenoxybenzyl ether;
(40) 0,0-dimethyl 0-(3-methyl-4-nitrophenyl) phosphorothioate;
(41) 2,2-dichlorovinyl dimethyl phosphate;
(42) 0,0-diethyl 0-(2-isopropyl-6-methyl-4-pyrimidinyl) phosphorothioate;

(43) (E)-0-2-isopropoxycarbonyl-1-methylvinyl 0-methyl ethylphosphoroamidothioate;
(44) 0,0-diethyl 0-(3,5,6-trichloro-2-pyridinyl) phosphorothioate;
(45) 0,0-dimethyl 0-(3,5,6-trichloro-2-pyridinyl) phosphorothioate;
(46) S-6-chloro-2,3-dihydro-2-oxo-1,3-oxazolo[4,5-b]pyridin-3-ylmethyl 0,0-dimethyl phosphorothioate;
(47) 5-methoxy-3-(2-methoxyphenyl)-1,3,4-oxadiazol-2(3H)-on;
(48) 2-isopropoxyphenyl N-methylcarbamate;
(49) 1-naphthyl N-methylcarbamate;
(50) 1-[(6-chloro-3-pyridinyl)methyl]-4,5-dihydro-N-nitro-1H-imidazole-2-amine;
(51) N-[(6-chloro-3-pyridinyl)methyl]-N'-cyano-N-methyl ethanimidamide;
(52) N-[(6-chloro-3-pyridinyl)methyl]-N-ethyl-N'-methyl-2-nitrovinylidenediamine;
(53) *Bacillus thuringiensis* protein; and
(54) *Bacillus sphericus* protein The composition of the invention may contain only one or a mixture of the insect growth-regulating active ingredient. In the latter case, the mixing ratio may be determined arbitrarily. The another insecticidal active ingredient may be added to the insect growth-regulating active ingredient at an arbitrary mixing ratio; generally 1:100 through 100:1, preferably 1:10 through 10:1 all at the ratio by weight. The amount of the insect growth-regulating active ingredient or that of the mixture of the insect growth-regulating active ingredient and the another insecticidal active ingredient (hereinafter referred to as the active ingredient) depends upon the type of the active ingredient, but may be generally 0.01 through 80% by weight, preferably 0.1 through 50% by weight based on the total weight of the composition of the invention. When the active ingredient is liquid or dissolved in a solvent, the amount of the liquid is generally 0.01 through 50% by weight, preferably 0.1 through 40% by weight based on the total weight of the composition of the invention.

Typical examples of the organic substance i.e. the constituent (b) contained in the composition of the invention, which has a solubility of not greater than 2% in water at 20° C. and a melting point of 35° through 100° C., are given below, although the constituent (b) is not limited to these examples. They include: saturated monohydric alcohols such as cetyl alcohol, stearyl alcohol, arachic alcohol, behenyl alcohol, carnaubyl alcohol, ceryl alcohol, cholianyl alcohol, myricyl alcohol, melissyl alcohol, and lacseryl alcohol; normal-chain fatty acids such as lauric acid, myristic acid, palmitic acid, margaric acid, stearic acid, arachic acid, behenic acid, lignoceric acid, cerotic acid, montanic acid, and melissic acid; n-alkans(paraffins) such as heneicosane, docosane, tricosane, tetracosane, pentacosane, hexacosane, heptacosane, octacosane, nonacosane, triacontane, hentriacontane, dotriacontane, tritriacontane, tetratriacontane, pentatriacontane, hexatriacontane, heptatriacontane, octatriacontane, nonatriacontane, and tetracontane; n-alkylbenzenes such as nonadecylbenzene, eicosylbenzene, heneicosylbenzene, docosylbenzene, tricosylbenzene, tetracosylbenzene, pentacosylbenzene, hexacosylbenzene, heptacosylbenzene, octacosylbenzene, nonacosylbenzene, and triacontylbenzene; alcohol esters of fatty acids such as tetradecyl stearate, hexadecyl stearate, heptadecyl stearate, octadecyl stearate, hexacosyl stearate, and triacontyl stearate; ethylene glycol esters such as ethylene glycol monopalmitate, ethylene glycol dipalmitate, ethylene glycol monomargarate, ethylene glycol dimargarate, ethylene glycol monostearate, and ethylene glycol distearate; tallow; lard; palm oil; hardened rapeseed oil; hardened castor oil; hardened whale oil; beeswax; purified lanolin; vaseline; urethane compounds having no isocyanate terminal obtained through reaction of polyoxyalkylene compounds and organic polyisocyanates, for example, Newpol T-240U (trade name by SANYO CHEMICAL INDUSTRIES, LTD.) and Toxanon JT-1(trade name by SANYO CHEMICAL INDUSTRIES, LTD.), Toxanon JT-4 (trade name by SANYO CHEMICAL INDUSTRIES, LTD.) and Toxanon JT-14 (trade name by SANYO CHEMICAL INDUSTRIES, LTD.) obtained by introducing benzene rings into polyoxyethylene polyoxypropylene glycol. The composition of the invention may contain only one of these organic substances or a mixture thereof.

The constituent (c) contained in the composition of the invention may be used with only one glycol or an arbitrary mixture of glycols. Polyethylene glycol used as the constituent (c) has an average molecular weight of not less than 1,000; preferably of 4,000 through 20,000 for the favorable solubility in water.

Polyoxyethylene polyoxypropylene glycol as the constituent (c) generally has 80% or greater of the ethylene oxide weight in molecule thereof and an average molecular weight of not less than 1,000 in the propylene oxide moiety.

Polyoxyethylene polyoxybutylene glycol and polyoxyethylene polyoxypropylene polyoxybutylene glycol as the constituent (c) generally have 80% or greater of the ethylene oxide weight in molecule thereof and an average molecular weight of not less than 1,000 in the butylene oxide or propylene oxide moiety.

Typical examples of the polyethylene glycol and polyoxyethylene polyoxypropylene glycol are polyethylene glycols having an average molecular weight of 1,000, 4,000, 6,000, 10,000 and 20,000 (hereinafter respectively referred to as PEG-1000, PEG-4000, PEG-6000, PEG-10000 and PEG-20000), Newpol PE-68 (trade name by SANYO CHEMICAL INDUSTRIES, LTD.; polyoxyethylene polyoxypropylene glycol having 80% of ethylene oxide weight in molecule thereof and an average molecular weight of 1,750 in the propylene oxide moiety), Newpol PE-78 (trade name by SANYO CHEMICAL INDUSTRIES, LTD.; polyoxyethylene polyoxypropylene glycol having 80% of ethylene oxide weight in molecule thereof and an average molecular weight of 2,050 in the propylene oxide moiety), Newpol PE-88 (trade name by SANYO CHEMICAL INDUSTRIES, LTD.; polyoxyethylene polyoxypropylene glycol having 80% of ethylene oxide weight in molecule thereof and an average molecular weight of 2,250 in the propylene oxide moiety), and Newpol PE-108 (trade name by SANYO CHEMICAL INDUSTRIES, LTD.; polyoxyethylene polyoxypropylene glycol having 80% of ethylene oxide weight in molecule thereof and an average molecular weight of 3,250 in the propylene oxide moiety).

The sum of the weight of constituent (b) and the weight of constituent (c) is generally 20 through 98%, preferably 25 through 95% based on the total weight of the composition of the invention. The amount of the constituent (b) is not less than 3% by weight based on the total weight of the composition of the invention.

The composition of the invention may further contain synergists, surface active agents, solvents, water-soluble carriers, mineral carriers, vegetable carriers, synthetic carriers, active carbon, water-soluble polymers other than the constituent (c), fragrance material, and coloring matter according to the requirements.

Typical examples of the synergists which may be contained in the composition of the invention are piperonyl butoxide, octachlorodipropyl ether, isobornyl thiocyanatoacetate, Syneprin 222, and Syneprin 500.

Surface active agents which may be contained in the composition are those for emulsifying or dispersing the active ingredient, and the like. Examples of the surface active agents are: anionic surface active agents such as alkylbenzenesulfonates, alkyl naphthalenesulfonates, lignin sulfonates, dialkyl sulfosuccinate, polyoxyethylene alkyl aryl ether sulfates, alkaline metal salts of carboxyl group-containing copolymers, and salts of fatty acid; and nonionic surface active agents such as polyoxyethylene alkyl ether, polyoxyethylene alkyl phenyl ether, polyoxyethylene styrylphenyl ether, polyoxyethylene alkyl ester, sorbitan alkyl ester, and polyoxyethylene sorbitain alkyl ester. Cationic surface active agents and ampholytic surface active agents may also be used, if necessary. The composition of the invention may contain only one surface active agent or a mixture of two or more surface active agents. When the surface active agent is used, the amount of the surface active agent is generally 0.1 through 30% by weight, preferably 1 through 20% by weight based on the total weight of the composition of the invention.

The composition may contain nonvolatile or scarcely volatile organic solvents. The solvents used for regulating the viscosity and preventing crystallization of the active ingredient should be those miscible homogeneously with the active ingredient. Typical examples of the solvent are: aromatic hydrocarbons such as phenylxylylethane, alkylbenzene, and methylnaphthalene; ketones; esters such as diisodecyl adipate, ditridecyl phthalate, and dialkylphthalate; vegetable oils; mineral oils; liquid paraffins; glycol ethers having the average molecular weight of about 200 through 600 and being in a liquid state at room temperatures, such as polyethylene glycol, polypropylene glycol, and polypropylene glycol methyl ether; and acetates of the glycol ethers. Specifically preferable are aromatic hydrocarbons such as phenylxylylethane, alkylbenzene, and methylnaphthalene; esters; glycol ethers; and acetates of the glycol ethers. The solvent may be added to the composition of the invention in order to improve the diffusion of the active ingredient in water or enhance the effects of the active ingredient irrespective of the melting point of the active ingredient. In such a case, those being miscible homogeneously with the active ingredient and having the specific gravity of not greater than 1.0 are preferable for floating the active ingredient to improve its diffusion in water. The amount of the solvent is generally 10 through 1,000% by weight, preferably 30 through 200% by weight based on the weight of active ingredient.

The composition of the invention may further contain silica (precipitated hydrated silicon dioxide) produced by wet process, calcined product of the silica produced by wet process, the silica produced by dry process, processed starch or calcium silicate. Examples of the silica produced by wet process are synthetic water-containing silicon oxides such as Tokusil GU-N, Tokusil U, Tokusil GU, and Tokusil N (trade names by Tokuyama Corp.) and Carplex #80, Carplex #67, Carplex #1120, Carplex #100, Carplex 22S, Carplex FPS-1, Carplex FPS-2, Carplex FPS-3, and Carplex FPS-4 (trade names by Shionogi & Co., Ltd.), Nipsil (trade name by Nihon Silica Corp.), and Ultrasil (trade name by Degussa Corp). The calcined product of the silica is obtained by calcining the above the silica produced by wet process at 700° through 900° C., preferably at 800° through 900° C. Commercially available calcined product of the silica, for example, Carplex CS-5, Carplex CS-7 (trade names by Shionogi & Co., Ltd.), or Finisil P-8 (trade name by Tokuyama Corp.) may be used as received. Examples of the silica produced by dry process used herein are light silicic anhydride prepared by dry process, such as AEROSIL 200 and AEROSIL 300 (trade names by Degussa Corp.). An example of calcium silicate is Florite R (trade name by Tokuyama Corp.), and an example of processed starch is Pineflow (trade name by Matsutani Chemical Co., Ltd).

Examples of the water-soluble carriers which may be added to the composition of the invention are urea, ammonium sulfate, lactose, sucrose, dextrin, salt, sodium sulfate, sodium tripolyphosphate, potassium pyrophosphate, sodium carbonate, sodium hydrogencarbonate, potassium carbonate, potassium hydrogencarbonate, maleic acid, citric acid, fumaric acid, and malic acid.

Examples of the mineral carriers which may be contained in the composition of the invention are kaolin, talc, pyrophylite, diatomaceous earth, montmorillonite, bentonite, activated clay, acid clay, attapulgite, and calcium carbonate.

Examples of the vegetable carriers which may be contained in the composition of the invention are wheat flour, woodmeal, cellulose powder, and starch.

The synthetic carriers which may be contained in the composition of the invention are silica produced by wet process, calcined product of the silica produced by wet process, silica produced by dry process, and calcium silicate.

Examples of the active carbon which may be contained in the composition of the invention are sawdust carbon, coconutshell carbon, and charcoal activated with a chemical such as zinc chloride, potassium sulfide, and potassium thiocyanate.

Examples of the water-soluble polymers which may be contained in the composition of the invention are hydroxylpropylcellulose, methylcellulose, gum arabic, sodium malginate, methylethylcellulose, polyvinyl alcohol, polyvinylpyrrolidone, hydroxypropylmethylcellulose, and carboxymethylcellulose.

The fragrance material which may be contained in the composition of the invention are isoamyl isovalerate, allyl cyclohexylpropionate, and 1-menthol specified in the Japanese Standard of Food Additives and/or the Cosmetics Materials Standard.

The coloring matter used in the invention may be those specified in the Japanese Standard of Food Additives.

The total amount of the water-soluble carriers, mineral carriers, vegetable carriers, synthetic carriers, active carbon, water-soluble polymers, fragrance material, and the coloring matter may be 0.1 through 70% by weight, preferably 0.5 through 50% by weight based on the total weight of the composition.

When the composition of the invention is used in water system to prevent breeding of or exterminate pests, it is preferable to add the mineral carrier, the vegetable carrier, the synthetic carrier and/or active carbon to the composition of the invention.

The composition of the invention may be prepared by the methods below: an mixture containing the components are obtained according to Process 1 including the steps of: sufficiently mixing all the constituents of the composition, and heating the mixture to specific temperature at which both constituent (b) and constituent (c) are molten, so as to melt constituent (b) and constituent (c); according to Process 2 including the steps of: sufficiently mixing the components other than constituent (b) and constituent (c), and adding a previously melted mixture of the constituent (b) and the constituent (c) to the mixture of the other components; or according to Process 3 including the steps of, heating and melting the active ingredient; mixing the melted active ingredient with a previously melted mixture of constituent (b) and constituent (c), and mixing other components with the mixture. Then the resulting mixture is poured into a mold or stretched to a plate, cooled and solidified, and then cut or crushed according to the requirements, so that final products of blocks, plates, and granules are obtained. The temperature required for melting constituent (b) and constituent (c) is not less than 50° C., preferably 60° through 120° C.

In the mixing process described above, Ribbon blenders, Henschel mixers, tumbling mixers, Readyge mixers, kneaders, V-mixing machines, and mixing tanks with stirrers can be used.

When the active ingredient is not molten at the temperature that constituent (b) and constituent (c) are molten, it is preferable that the above process is conducted after the active ingredient itself or a mixture of the active ingredient and powder additives such as a surface active agent is pulverized with a dry pulverizer such as a jetmizer, a pin mill, and a hammer mill to the average particle diameter of not greater than 30 μm, preferably not greater than 10 μm.

When the active ingredient can not be mixed with constituent (b) and constituent (c) homogeneously, a powerful stirrer such as a homogenizer is used to disperse the active ingredient sufficiently.

Examples of the mold used in the processes of the composition of the invention are molds having a variety of shapes such as discs, hearts, pillows, lenses, fingers, corns, columns, domes, hemispheres, stars, capsules, and cubes. Examples of the tolls used in the cutting, crushing and granulating process of the invention are sharp blades such as cutters and knives and crushers having a variety of shapes.

The composition containing two or more active ingredients may be formed to tablets or pills having a double-layered or multi-layered structure, which includes a first layer containing one active ingredient and constituents (b) and (c) and a second layer containing the other active ingredient and constituents (b) and (c). Such structure is especially useful when an insect growth-regulating active ingredient is used together with another insecticidal active ingredient whose mixing with the insect growth-regulating active ingredient is prohibited.

The weight per one block or plate of the composition of the invention is 1 through 2,000 g, preferably 10 through 1,000 g, more preferably 25 through 100 g. When the composition of the invention is formed to granules, the preferable average particle diameter for easy handling is 100 through 5,000 μm, preferably 200 through 3,000 μm. The preferable preparation from the view point of the efficacy is blocks or plates having the unit weight of 10 through 1,000 g, preferably 25 through 500 g.

The composition of the invention thus prepared is applied, for example, to gutters, ditches, sewers, rivers, channels, the sea, ponds, swamps, canals, puddles, rice paddies, and water inlets into rice paddies, drainages of bath tubs, and flush toilets.

When the composition of the invention is applied to gutters, ditches, sewers, rivers, channels, the sea, ponds, swamps, canals, puddles, rice paddies, and water inlets into rice paddies, the composition may be used as it is, or wrapped in a water-soluble film and used. The composition may be thrown into the above water systems from the ground, applied using a granular applicator or tablet applicator using a ship or boat in the water systems, using a chopper, an airplane, or a radio-controlled plane from the air. The composition of the invention may be put in nylon mesh-bags, which are fixed to specific places for steady application.

When the composition of the invention is applied to water inlets into rice paddies, drainages of bath tubs, and flush toilets, the composition may be put in nylon mesh-bags or plastic vessels having apertures through which water passes.

The amount of application of the composition may vary depending upon the types and quantities of the active ingredient and the places for application. When the composition of the invention is applied to drainages of bath tubs or flush toilets, the application amount is 1 through 500 g, preferably 5 through 100 g. When the composition of the invention is applied to water inlets into rice paddies, the amount is 50 through 5,000 g, preferably 100 through 2,000 g. When the composition of the invention is applied to gutters, ditches, sewers, rivers, channels, the sea, ponds, swamps, canals, puddles, or rice paddies, the amount of the active ingredient is 0.0001 through 10,000 g, preferably 0.001 through 1,000 g per 1 $m^3$ of water or 1 $m^3$ of the water flow per hour.

The composition of the invention is effective for exterminating Dipteran pests, which are bred in the water systems or the surroundings of the water systems, and includes midges such as *Chironomus darsalis*, *Orthocladius akamusi*, *Chironomus plumosus*, *Chironomus Küensis*, *Glyptotendipes pallens*, *Cricotopus bicinctus*, moth flies such as *Psychoda alternata* and *Telmatoscopus albipunctatus*, hompbacked flies such as *Dohrniphora cornuta* and *Megaselia spiracularis*, house mosquitoes like *Culex pipiens pallens* and *Culex pipiens Coquillett molestus*, Aedes mosquitoes such as *Aedes albopictus* and *Aedes togoi* THEOBALD, and Anopheles mosquitoes such as *Anopheles hyrcanus sinensis*. The composition of the invention has also effects on: Hemiptera pests including Delphacidae (leaf hoppers) such as *Laodelphax striatellus*, *Nilaparvata lugens*, and *Sogatella furcifera*, and Cicadelloidea (leaf hoppers) such as *Nephotettix cincticeps* and *Nephotettix virescens*; Coleopteran such as *Lissorphoptrus oryzae*; and pests in paddy field such as *Chilo suppressalis*, *Cnaphalocrocis medinalis*, stinkbugs, and locusts.

The invention will be described more in detail with preparation examples, comparative preparation examples and test examples although the invention is not restricted to these examples in any sense. In the preparation examples and comparative preparation examples, the term 'parts' denotes 'parts by weight'.

Preparation Example 1

Five parts of compound (3), 10 parts of phenylxylylethane, 5 parts of Sorpol 3598 (surface active agent manufactured by Toho Chemicals Co., Ltd.), 40 parts of PEG-20000 and 40 parts of Newpol T-240 U were put into a beaker, and mixed sufficiently to a homogeneous solution with heating at 80° C. The homogeneous solution mixture thus obtained was poured into a plastic vessel having a diameter of approximately 5 cm and cooled and solidified to give disk-shaped blocks having a unit weight of 50 g. The blocks were then cut with a universal knife into cube formulation having a unit weight of 1 g (approximately 1 cm in each side).

Preparation Example 2

Cube formulation having a unit weight of 1 g was prepared in the same process as Preparation Example 1 except that 40 parts of Toxanon JT-1 was used in place of 40 parts of Newpol T-240 U.

Preparation Example 3

Cube formulation having a unit weight of 1 g was prepared in the same process as Preparation Example 1 except that 5 parts of the compound (3), 10 parts of phenylxylylethane, 5 parts of Sorpol 3598, 5 parts of PEG-20000, and 75 parts of Toxanon JT-1 were used.

Preparation Example 4

Cube formulation having a unit weight of 1 g was prepared in the same process as Preparation Example 1 except that 5 parts of the compound (3), 5 parts of phenylxylylethane, 5 parts of Sorpol 3598, 60 parts of PEG-20000, and 25 parts of Toxanon JT-1 were used.

Preparation Example 5

Cube formulation having a unit weight of 1 g was prepared in the same process as Preparation Example 1 except that 5 parts of compound (3), 5 parts of Sorpol 3598, 45 parts of PEG-20000, and 45 parts of Toxanon JT-1 were used.

Preparation Example 6

Cube formulation having a unit weight of 1 g was prepared in the same process as Preparation Example 1 except that 5 parts of compound (3), 10 parts of phenylxylylethane, 2.5 parts of Sorpol 3598, 42.5 parts of PEG-20000, and 40 parts of Toxanon JT-1 were used.

Preparation Example 7

Cube formulation having a unit weight of 1 g was prepared in the same process as Preparation Example 1 except that 5 parts of compound (3), 10 parts of phenylxylylethane, 42.5 parts of PEG-20000, and 42.5 parts of Toxanon JT-1 were used.

Preparation Example 8

Cube formulation having a unit weight of 1 g was prepared in the same process as Preparation Example 1 except that 5 parts of compound (3), 10 parts of phenylxylylethane, 5 parts of Sorpol 3598, 35 parts of PEG-20000, 35 parts of Toxanon JT-1, and 10 parts of diatomaceous earth were used.

Preparation Example 9

Cube formulation having a unit weight of 1 g was prepared in the same process as Preparation Example 1 except that 5 parts of the compound (3), 10 parts of phenylxylylethane, 5 parts of Sorpol 3598, 35 parts of PEG-20000, 35 parts of Toxanon JT-1, and 10 parts of lactose were used.

Preparation Example 10

Cube formulation having a unit weight of 1 g was prepared in the same process as Preparation Example 1 except that 5 parts of compound (3), 10 parts of phenylxylylethane, 5 parts of Sorpol 3598, 40 parts of Newpol PE-108, and 40 parts of Toxanon JT-1 were used.

Preparation Example 11

Cube formulation having a unit weight of 1 g was prepared in the same process as Preparation Example 1 except that 5 parts of compound (3), 10 parts of phenylxylylethane, 5 parts of Sorpol 3598, 40 parts of PEG-20000, and 40 parts of stearic acid were used.

Preparation Example 12

Cube formulation having a unit weight of 1 g was prepared in the same process as Preparation Example 1 except that 5 parts of compound (3), 10 parts of phenylxylylethane, 5 parts of Sorpol 3598, 40 parts of PEG-20000, and 40 parts of stearyl alcohol were used.

Preparation Example 13

Ten parts of compound (3), 20 parts of phenylxylylethane, 5 parts of Sorpol 3598, 5 parts of stearic acid, and 60 parts of PEG-20000 were put into a beaker and mixed sufficiently to a homogeneous solution with heating at 90° C. The homogeneous solution mixture thus obtained was poured into a plastic vessel having a diameter of approximately 5 cm and cooled and solidified to give a columnar formulation having a unit weight of 100 g.

Preparation Example 14

Columnar formulation having a unit weight of 100 g was prepared in the same process as Preparation Example 13 except that 10 parts of compound (3), 20 parts of phenylxylylethane, 5 parts of Sorpol 3598, 10 parts of stearic acid, and 55 parts of PEG-20000 were used.

Preparation Example 15

Columnar formulation having a unit weight of 100 g was prepared in the same process as Preparation Example 13 except that 10 parts of compound (3), 20 parts of phenylxylylethane, 5 parts of Sorpol 3598, 15 parts of stearic acid, and 50 parts of PEG-20000 were used.

Preparation Example 16

Columnar formulation having a unit weight of 100 g was prepared in the same process as Preparation Example 13 except that 10 parts of compound (3), 20 parts of phenylxylylethane, 5 parts of Sorpol 3598, 25 parts of stearic acid, and 40 parts of PEG-20000 were used.

Preparation Example 17

Columnar formulation having a unit weight of 100 g was prepared in the same process as Preparation Example 13 except that 10 parts of compound (3), 20 parts of phenylxylylethane, 5 parts of Sorpol 3598, 35 parts of stearic acid, and 30 parts of PEG-20000 were used.

Preparation Example 18

Columnar formulation having a unit weight of 100 g was prepared in the same process as Preparation Example 13 except that 10 parts of compound (3), 10 parts of phenylxylylethane, 10 parts of Sorpol 3598, 5 parts of stearic acid, and 65 parts of PEG-20000 were used.

Preparation Example 19

Columnar formulation having a unit weight of 100 g was prepared in the same process as Preparation Example 13 except that 10 parts of compound (3), 10 parts of phenylxylylethane, 10 parts of Sorpol 3598, 10 parts of stearic acid, and 60 parts of PEG-20000 were used.

Preparation Example 20

Columnar formulation having a unit weight of 100 g was prepared in the same process as Preparation 13 except that 10 parts of compound (3), 20 parts of phenylxylylethane, 5 parts of Sorpol 3598, 6.5 parts of stearic acid, and 58.5 parts of PEG-20000 were used.

Preparation Example 21

Columnar formulation having a unit weight of 100 g was prepared in the same process as Preparation Example 13 except that 10 parts of compound (3), 20 parts of phenylxylylethane, 5 parts of Sorpol 3598, 8 parts of stearic acid, and 57 parts of PEG-20000 were used.

Preparation Example 22

Columnar formulation having a unit weight of 100 g was prepared in the same process as Preparation Example 13 except that 10 parts of compound (3), 20 parts of phenylxylylethane, 5 parts of Sorpol 3598, 12 parts of stearic acid, and 53 parts of PEG-20000 were used.

Preparation Example 23

Columnar formulation having a unit weight of 100 g was prepared in the same process as Preparation Example 13 except that 10 parts of compound (3), 20 parts of phenylxylylethane, 5 parts of Sorpol 3598, 13 parts of stearic acid, and 52 parts of PEG-20000 were used.

Preparation Example 24

Columnar formulation having a unit weight of 100 g was prepared in the same process as Preparation Example 13 except that 10 parts of compound (3), 20 parts of phenylxylylethane, 5 parts of Sorpol 3598, 14 parts of stearic acid, and 51 parts of PEG-20000 were used.

Preparation Example 25

Columnar formulation having a unit weight of 100 g was prepared in the same process as Preparation Example 13 except that 5 parts of the compound (3), 10 parts of the compound (24), 10 parts of phenylxylylethane, 5 parts of Sorpol 3598, 10 parts of stearic acid, and 60 parts of PEG-20000 were used.

Preparation Example 26

2.5 Parts of compound (3), 2.5 parts of phenylxylylethane, 5 parts of Sorpol 3598, 5 parts of stearic acid, and 25 parts of PEG-20000 were put into a beaker and mixed sufficiently to a homogeneous solution with heating at 90° C. Forty grams of the homogeneous solution mixture thus obtained were poured into a plastic vessel having a diameter of approximately 5 cm and cooled and solidified. Ten parts of compound (40), 5 parts of Sorpol 355 (surface active agent manufactured by Toho Chemicals Co., Ltd.), 8 parts of stearic acid, and 37 parts of PEG-20000 were put into a beaker and mixed sufficiently to a homogeneous solution with heating at 90° C. The second homogeneous solution mixture was then poured into the above plastic vessel and cooled and solidified to give columnar formulation having a double-layered structure and the unit weight of 100 g.

Preparation Example 27

Ten parts of compound (3), 10 parts of phenylxylylethane, 5 parts of Sorpol 3598, 13 parts of stearic acid, and 52 parts of PEG-20000 were put into a beaker and mixed sufficiently to a homogeneous solution with heating at 90° C. After 10 parts of Tokusil GU-N (silica produced by wet process, and manufactured by Tokuyama Corp.) were added and dispersed in the homogeneous solution, the resultant mixture was poured into a paper vessel having the diameter of 5 cm and cooled and solidified to give columnar formulation having a unit weight of 100 g.

Preparation Example 28

Columnar formulation having a unit weight of 100 g was prepared in the same process as Preparation Example 27 except that 10 parts of Attapulgite LVM25/50 (calcined attapulgite manufactured by ENGLHARD Corp.; particle diameter: 300 through 600 µm) was used in place of 10 parts of Tokusil GU-N.

Preparation Example 29

Ten parts of the compound (3), 10 parts of phenylxylylethane, 5 parts of Sorpol 3598, 8 parts of stearic acid, and 57 parts of PEG-20000 were put into a beaker and mixed sufficiently to a homogeneous solution with heating at 90° C. After 10 parts of Carborafin (active carbon manufactured by Takeda Chemical Industries Ltd.) were added and dispersed in the homogeneous solution, the resulting mixture was poured into a paper vessel having the diameter of 5 cm, and cooled and solidified to give columnar formulation having the unit weight of 100 g.

Preparation Example 30

Ten parts of compound (3), 20 parts of phenylxylylethane, 5 parts of Sorpol 3598, 10 parts of stearic acid, and 45 parts of PEG-20000 were put into a beaker and mixed sufficiently to a homogeneous solution with heating at 90° C. After 10 parts of powdery 3,000 IU/mg *Bacillus thuringiensis* var. *israelensis* were added and dispersed in the homogeneous solution, the mixture was poured into a paper vessel having the diameter of 5 cm and cooled and solidified to give columnar formulation having the unit weight of 100 g.

Comparative Preparation Example 1

0.5 Part of compound (3), 1 part of phenylxylylethane, and 1 part of Sorpol 3598 were mixed sufficiently to a homogeneous solution.

Granules were prepared by homogeneously impregnating 97.5 parts of Ishikawa Light Pesticide No. 3 (granular carrier (pumice) by Ishikawa Light Industries Ltd.) with the solution.

Comparative Preparation Example 2

Cube formulation having a unit weight of 1 g was prepared in the same process as Preparation Example 1 except that 5 parts of a compound (3), 10 parts of phenylxylylethane, 5 parts of Sorpol 3598, and 80 parts of PEG-20000 were used.

Comparative Preparation Example 3

Columnar formulation having a unit weight of 100 g was prepared in the same process as Preparation Example 13 except that 10 parts of compound (3), 20 parts of phenylxylylethane, 5 parts of Sorpol 3598, and 65 parts of PEG-20000 were used.

The Test Examples were shown below.

Test Example 1

Five liters of water (20° C.) were put into a 5-liter beaker 1 and stirred with a stirrer 2 at a rotating speed of 450 rpm as illustrated in FIG. 1. While water (20° C.) was introduced into the beaker 1 with a roller pump 3 at a speed of 1.2 liters/minute, water was discharged from the beaker 1 at the same speed of 1.2 liters/minute in the same method. After constructing the system, each 1 g of Preparation Examples 1, 2, 4–9, 11, 12 and Comparative Preparation Example 2, and 10 g of Comparative Preparation Example 1 were then applied to the 5-liter beaker 1, respectively. After application, water discharged from the beaker was collected, and the time-course variation in concentration of the active ingredient was analyzed by gas chromatography.

Table 1 shows results of the analysis. Larvae (wrigglers) of *Culex pipiens pallens* were placed in the discharged water and the inhibition of emergence was measured. The results are shown in Table 2.

TABLE 1

| | Concentration of active ingredient in water (ppb) | | |
|---|---|---|---|
| | after 10 min. | after 60 min. | after 120 min. |
| Preparation Example 1 | 265 | 275 | 219 |
| Preparation Example 2 | 283 | 252 | 187 |
| Preparation Example 4 | 164 | 215 | 153 |
| Preparation Example 5 | 145 | 176 | 171 |
| Preparation Example 6 | 99 | 89 | 133 |
| Preparation Example 7 | 17 | 33 | 45 |
| Preparation Example 8 | 116 | 169 | 161 |
| Preparation Example 9 | 91 | 113 | 116 |
| Preparation Example 11 | 23 | 17 | 5 |
| Preparation Example 12 | 20 | 10 | 6 |
| Comp. Preparation Example 1 | 427 | 61 | 0 |
| Comp. Preparation Example 2 | 771 | 230 | 0 |

TABLE 2

| | Inhibition of emergence (%) | | |
|---|---|---|---|
| | after 10 min. | after 60 min. | after 120 min. |
| Preparation Example 1 | 100 | 100 | 100 |
| Preparation Example 2 | 100 | 100 | 100 |
| Preparation Example 4 | 100 | 100 | 100 |
| Preparation Example 5 | 100 | 100 | 100 |
| Preparation Example 6 | 100 | 100 | 100 |
| Preparation Example 7 | 100 | 100 | 100 |
| Preparation Example 8 | 100 | 100 | 100 |
| Preparation Example 9 | 100 | 100 | 100 |
| Preparation Example 11 | 100 | 100 | 100 |
| Preparation Example 12 | 100 | 100 | 100 |
| Comp. Preparation Example 1 | 100 | 100 | 0 |
| Comp. Preparation Example 2 | 100 | 100 | 0 |

Test Example 2

After a 2-liter plastic vessel 5 having a stirrer therein was covered with a mesh-bag 6 whose end was located at a scale of 1 liter as illustrated in FIG. 2, 1900 cc of ion-exchanged water 7 was introduced into the vessel 5. Each formulation 8 (100 g) obtained by Preparation Examples 13–19 and Comparative Preparation Example 3 was placed on the mesh-bag 6, and the water 7 was stirred with the magnetic stirrer at 1,400 rpm. After a fixed time period, 3 ml of the water was sampled from the approximate center of the vessel with a whole pipet. The concentration of the active ingredient was analyzed by gas chromatography, and the dissolution rate was calculated. The results are shown in Table 3.

Test 3

|  | Dissolution rate (%) | | | |
|---|---|---|---|---|
|  | after 1 day | after 2 days | after 5 days | after 7 days |
| Preparation Example 13 | 32.2 | 39.6 | 53.4 | 59.8 |
| Preparation Example 14 | 8.0 | 11.3 | 18.1 | 21.9 |
| Preparation Example 15 | 3.5 | 4.5 | 6.9 | 7.8 |
| Preparation Example 16 | 2.9 | 3.8 | 5.1 | 6.6 |
| Preparation Example 17 | 1.0 | 1.2 | 1.4 | 1.7 |
| Preparation Example 18 | 17.5 | 23.6 | 32.4 | 36.8 |
| Preparation Example 19 | 8.1 | 11.0 | 15.7 | 17.4 |
| Comp. Preparation Example 3 | 100.0 | 100.0 | 100.0 | 100.0 |

Test Example 3

A sewer (width: 11.6 m; whole length: approximately 1.1 km) shown in FIG. 3 was used for the test. The depth of water in the sewer was 22.5 cm on average. The flow rate was determined to be 40 m/min by measuring a time period that it takes for foamed polystyrene powder floating on this surface of water to travel a fixed distance (10 m). The flow per hour was thus approximately 6,000 t. Two formulation 9 obtained by Preparation Example 13 were put in the stocking. Fifteen stockings, each including two formulations, were respectively attached to two ropes 10 and soaked in the water. The ropes 10 spanned the width of the sewer at the upper-most stream and the middle position of the stream.

Three stockings were attached to each end of the width-spanning ropes, and the other nine stockings were attached to the ropes 10 at equal intervals. After two hours, water was collected at five positions in the lower-most stream shown in FIG. 3 (numerals 1, 2, 3, 4, 5 show the sampling positions). At this moment, the formulation 9 was slightly dissolved although for the most part still remained in the stockings. Hexane was added twice (80 ml for the first time and 50 ml for the second time) to 250 ml of the water, and shaken for distribution (10 minutes×twice). The hexane phase was dehydrated and filtered with a Kiriyama filter with mirabilite (anhydrous sodium sulfate) mounted thereon, concentrated under reduced pressure with a rotary evaporator in a warm bath of not greater than 40° C. The concentration of the active ingredient was then determined by gas chromatography. The results are shown in Table 4.

Twenty pupae of midges were collected from the middle position of the sewer on the third day and the seventh day after the application of the formulation, respectively and put into a cup. After 3 days, observation of the pupae in the plastic cup showed no emergence.

TABLE 4

| Sampling position | Concentration of the active ingredient (ppb) |
|---|---|
| 1 | 10.9 |
| 2 | 5.5 |
| 3 | 8.8 |
| 4 | 7.8 |
| 5 | 6.2 |

The above results showed the slow release of the active ingredient and the substantially homogeneous diffusion of the active ingredient in water.

Test Example 4

A channel (width: 1.7 m) shown in FIG. 4 was used for this test. The depth of water in the channel was 0.2 m and the flow rate was 45 m/min.

Ten formulations obtained from Preparation Examples 15, 23, 24 and Comparative Preparation Example 3 were respectively put in stockings 16. The stockings 16, including their respective formulations 15, were attached to a rope 17 spanning the width of the channel and soaked in the water. The stockings 16 were taken out of the water at various time points and the weight of the remaining formulations 15 was measured. The remaining rates of the formulations are shown in Table 5.

TABLE 5

|  | Remaining rate of formulation (%) | | | | | |
|---|---|---|---|---|---|---|
|  | after 1 day | after 2 days | after 3 days | after 4 days | after 5 days | after 6 days |
| Pre. Ex. 15 | 91.5 | 69.3 | 53.3 | 46.5 | 33.5 | 27.8 |
| Pre. Ex. 23 | 85.5 | 42.5 | 22.8 | 17.3 | 11.0 | 10.8 |
| Pre. Ex. 24 | 94.5 | 89.0 | 55.8 | 35.5 | 30.5 | 29.5 |
| Com. Pre. Ex. 3 | 0.0 |  |  |  |  |  |

The above results showed the slow release of the composition of the invention in running water systems.

Test Example 5

A channel (width: 1.7 m) shown in FIG. 4 was used for this test. The depth of water in the channel was 0.2 m and the flow rate was 45 m/min.

Ten formulations 15 obtained by Preparation Examples 25 and 26 were respectively put in a stocking 16. The stockings 16 with the respective formulations 15 therein were attached to a rope 17 spanning the width of the channel and soaked in the water. On the 14th day after the application of the formulation, twenty pupae of midges were collected at a position 500-meter downstream from the position of the application and put in a plastic cup. After 3 days, the pupae showed no emergence.

Test Example 6

After a 2-liter plastic vessel having a stirrer therein was covered with a mesh-bag whose end was located at a scale of 1 liter as illustrated in FIG. 2, 1900 cc of ion-exchanged water was introduced into the vessel. Each formulation (100 grams) obtained by Preparation Examples 27–29 was placed on the mesh-bag, and the water was stirred with the magnetic stirrer at 1,400 rpm. After three days, 3 ml of the water was sampled from the approximate center of the vessel with a whole pipet. The concentration of the active ingredient was analyzed by gas chromatography, and the dissolution rate was calculated. The results are shown in Table 6.

TABLE 6

|  | Dissolution rate (%) |
| --- | --- |
| Preparation Example 27 | 25.0 |
| Preparation Example 28 | 7.8 |
| Preparation Example 29 | 5.3 |

The composition of the invention is a labor- and cost-saving composition because it releases an active ingredient gradually, and exterminates harmful and/or offensive pests and prevents the breeding thereof in water systems over a long time.

BRIEF DESCRIPTION OF THE DRAWINGS

FIG. 1 illustrates experimental arrangements used in Test Example 1.

FIG. 2 illustrates experimental arrangements used in Test Examples 2 and 6.

FIG. 3 is a plan view showing a sewer used in Test Example 3.

FIG. 4 is a plane view showing the channel used in Test Examples 4 and 5.

Figure 1:
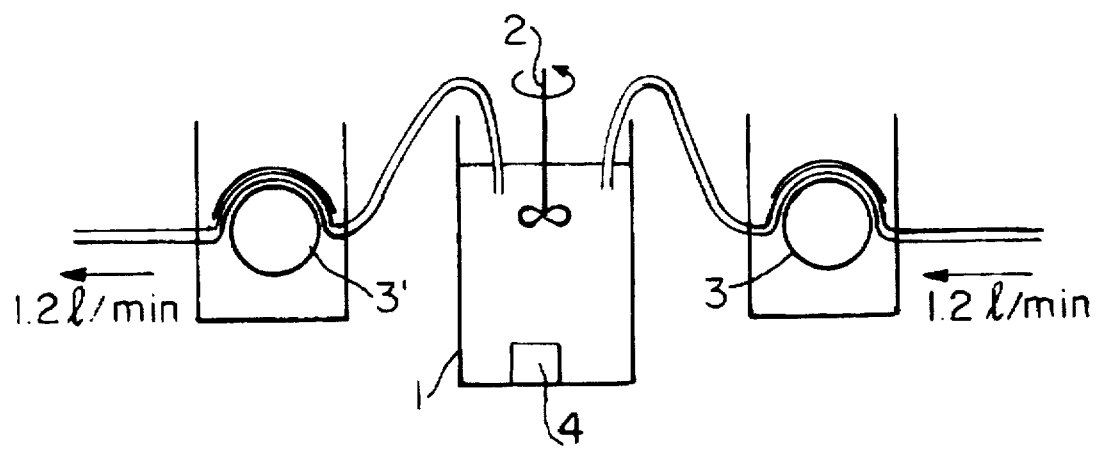
FIG. 1
Figure 2:
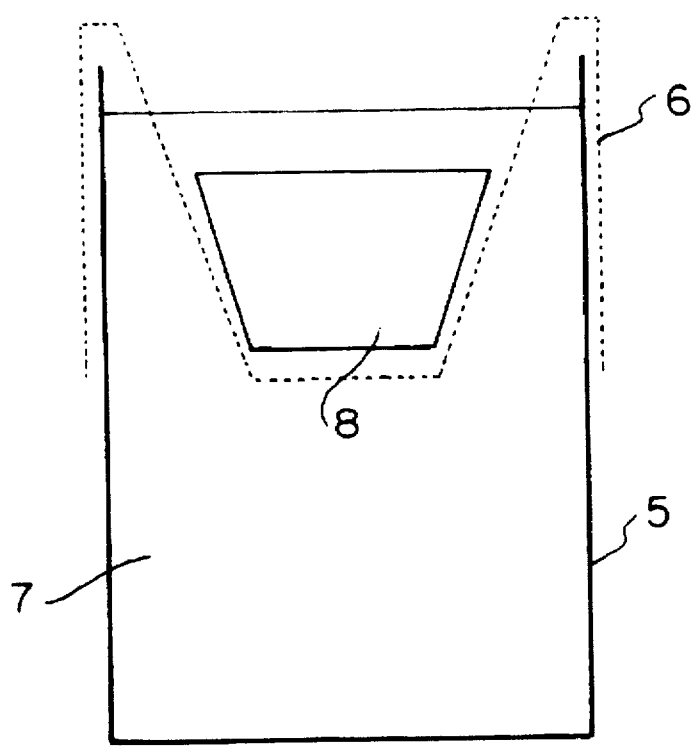
FIG. 2
Figure 3:
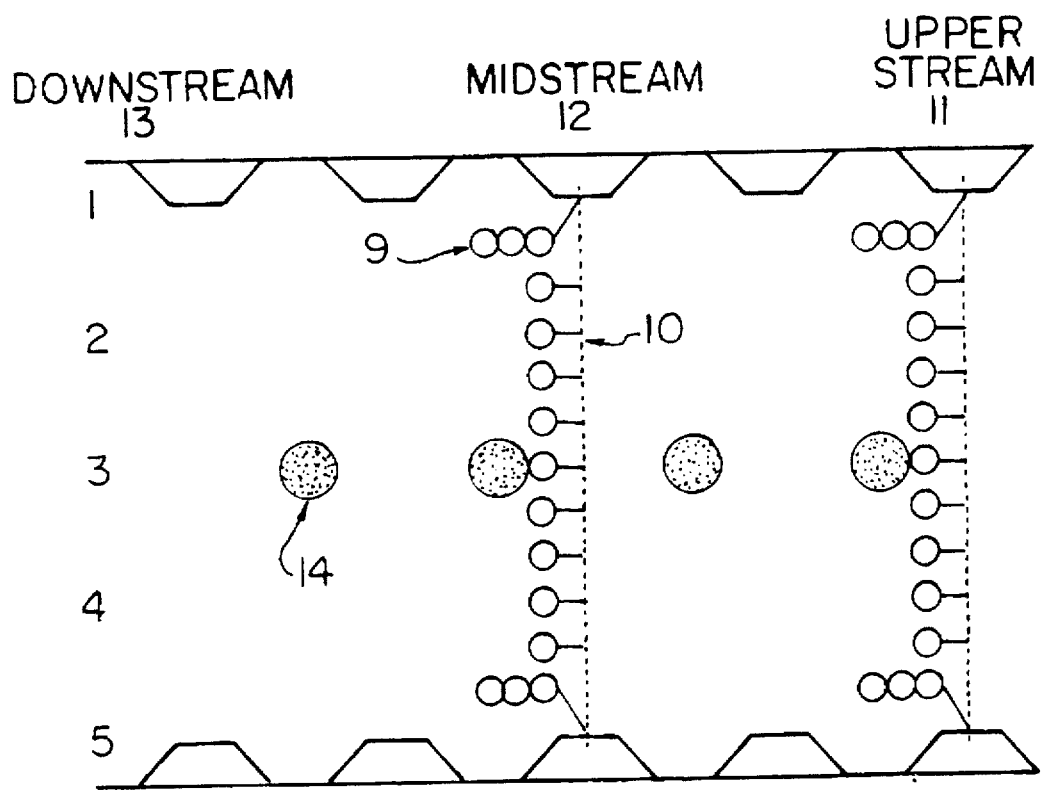
FIG. 3
Figure 4:
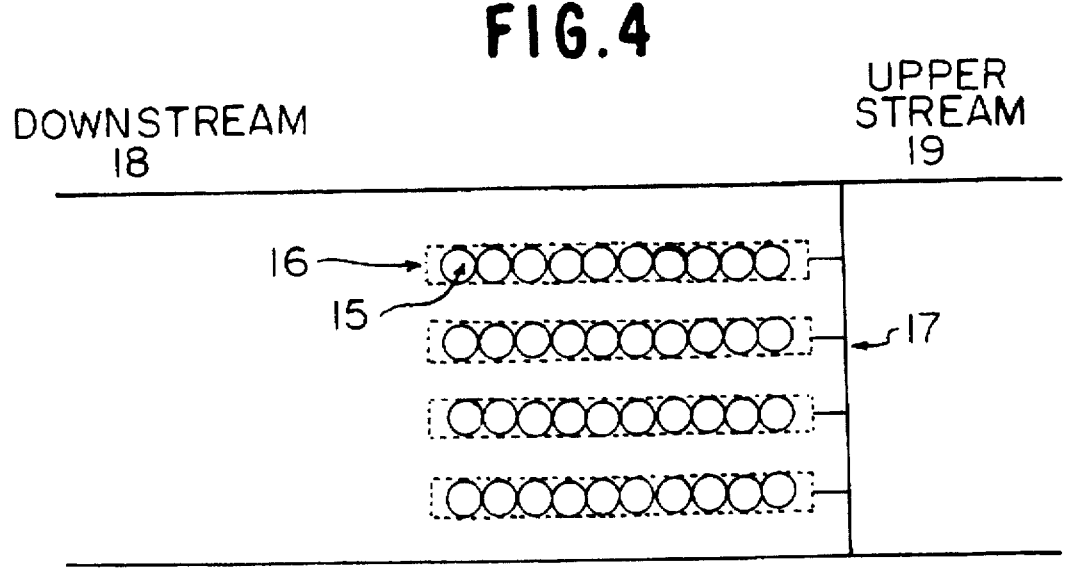
FIG. 4

What is claimed is:

1. A solid insect growth regulating composition having prolonged action for exterminating and/or preventing breeding of pests in water systems comprising:

(a) an insect growth-regulating active ingredient;

(b) an organic substance having a solubility of not greater than 2% in water at 20° C. and a melting point of 35° C. to 100° C., wherein the organic substance is selected from the group consisting of a saturated monohydric alcohol, a normal-chain fatty-acid, an n-alkan, an n-alkylbenzene, an alcohol ester of a fatty acid, an ethylene glycol ester, tallow, lard, palm oil, hardened rapeseed oil, hardened castor oil, hardened whale oil, beeswax, purified lanolin, vaseline, and a urethane compound having no isocyanate terminal obtained through reaction of polyoxyalkylene compounds and organic polyisocyanates; and (c) a glycol having a melting point of 35° C. to 100° C. selected from the group consisting of polyethylene glycol having average molecular weight of not less than 1,000, polyoxyethylene polyoxypropylene glycol having 80% or greater of the ethylene oxide weight in the molecule thereof and average molecular weight of not less than 1,000 in the propylene oxide moiety, polyoxyethylene polyoxybutylene glycol having 80% or greater of the ethylene oxide weight in the molecule thereof and average molecular weight of not less than 1,000 in the butylene oxide moiety, and polyoxyethylene polyoxypropylene polyoxybutylene glycol having 80% or greater of the ethylene oxide weight in the molecule thereof and the average molecular weight of not less than 1,000 in the butylene oxide moiety or propylene oxide moiety, wherein (i) the weight of constituent (b) is equal to or greater than 3% based on the total weight of said solid insect growth regulating composition, (ii) the sum of the weights of constituent (b) and constituent (c) ranges from 20% to 98% based on the total weight of said solid insect growth regulating composition, and (iii) constituent (b) and constituent (c) are added in molten form and then cooled to form a solid during the manufacturing process of said solid insect growth regulating composition.

2. The solid insect growth regulating composition according to claim 1, wherein the insect growth-regulating active ingredient is an insect juvenile hormone-like compound.

3. The solid insect growth regulating composition according to claim 1, wherein the insect growth-regulating active ingredient is Pyriproxyfen.

4. A solid insect growth regulating composition having prolonged action for exterminating and/or preventing breeding of pests in water systems comprising:

(a) an insect growth-regulating active ingredient and another insecticidal active ingredient;

(b) an organic substance having a solubility of not greater than 2% in water at 20° C. and a melting point of 35° C. to 100° C., wherein the organic substance is selected from the group consisting of a saturated monohydric alcohol, a normal-chain fatty-acid, an n-alkane, an n-alkylbenzene, an alcohol ester of a fatty acid, an ethylene glycol ester, tallow, lard, palm oil, hardened rapeseed oil, hardened castor oil, hardened whale oil, beeswax, purified-lanolin, vaseline, and a urethane compound having no isocyanate terminal obtained through reaction of polyoxyalkylene compounds and organic polyisocyanates; and (c) a glycol having a melting point of 35° C. to 100° C. selected from the group consisting of polyethylene, glycol having average molecular weight of not less than 1,000, polyoxyethylene polyoxypropylene glycol having 80% or greater of the ethylene oxide weight in the molecule thereof and average molecular weight of not less than 1,000 in the propylene oxide moiety; polyoxyethylene polyoxybutylene glycol having 80% or greater of the ethylene oxide weight in the molecule thereof and the average molecular weight of not less than 1,000 in the butylene oxide moiety and polyoxyethylene polyoxypropylene polyoxybutylene glycol having 80 % or greater of the ethylene oxide weight in the molecule thereof and the average molecular weight of not less than 1,000 in the butylene oxide moiety propylene oxide moiety.

5. The solid insect growth regulating composition according to claim 4, wherein the insect growth-regulating active ingredient is an insect juvenile hormone-like compound.

6. The solid insect growth regulating composition according to claim 4, wherein the insect growth-regulating active ingredient is an insect juvenile hormone-like compound, and the other insecticidal active ingredient is selected from the group consisting of a pyrethroid, an organophosphorsus compound, and an insecticidal protein.

7. The solid insect growth regulating composition according to claim 4, wherein the insect growth-regulating active ingredient is Pyriproxyfen.

8. The solid insect growth regulating composition according to claim 4, wherein the insect growth-regulating active ingredient is Pyriproxyfen, and the other insecticidal active ingredient is selected from the group consisting of a pyrethroid, an organophosphorus compound, and an insecticidal protein.

9. A method for controlling harmful and/or offensive pests in a water system comprising placing in said water system the solid insect growth regulating composition according to claim 1.

10. A method for controlling harmful and/or offensive pests using the solid insect growth regulating composition according to claim 2.

11. A method for controlling harmful and/or offensive pests using the solid insect growth regulating composition according to claim 3.

12. A method for controlling harmful and/or offensive pests using the solid insect growth regulating composition according to claim 4.

13. A method for controlling harmful and/or offensive pests using the solid insect growth regulating composition according to claim 5.

14. A method for controlling harmful and/or offensive pests using the solid insect growth regulating composition according to claim 6.

15. A method for controlling harmful and/or offensive pests using the solid insect growth regulating composition according to claim 7.

16. A method for controlling harmful and/or offensive pests using the solid insect growth regulating composition according to claim 8.

* * * * *